US005720977A

United States Patent [19]

Deghenghi

[11] Patent Number: 5,720,977
[45] Date of Patent: Feb. 24, 1998

[54] ORAL WATER SOLUBLE PHARMACEUTICAL COMPOSITIONS CONTAINING ESTRONE COMPOUND AND CALCIUM SALT

[76] Inventor: Romano Deghenghi, Cheseaux Dessus B1, St. Cergue, Switzerland

[21] Appl. No.: 592,377

[22] PCT Filed: Jul. 26, 1994

[86] PCT No.: PCT/EP94/02465

§ 371 Date: Feb. 1, 1996

§ 102(e) Date: Feb. 1, 1996

[87] PCT Pub. No.: WO95/07701

PCT Pub. Date: Mar. 23, 1995

[30] Foreign Application Priority Data

Sep. 17, 1993 [IT] Italy .................. M193A2014

[51] Int. Cl.$^6$ ............... A61K 9/08; A61K 9/16; A61K 9/20; A61K 9/46
[52] U.S. Cl. .............. 424/466; 424/464; 424/465; 424/489; 514/874; 514/770; 514/784
[58] Field of Search ............... 424/464, 465, 424/466, 489; 514/874, 770, 784

[56] References Cited

U.S. PATENT DOCUMENTS 5,004,651  4/1991  Becker .................. 424/465

OTHER PUBLICATIONS

Ettinger B. et al., "Calcium enhances the bone–sparing effects of low–dosage estrogen in postmenopausal women", Osteoporosis Int. (United Kingdom), 1993, vol. 3, Suppl. 1, pp. 157–158.

Geenant H.K. et al., "Effect of estrone sulfate on postmenopausal bone loss" Obstetric & Gynecology (USA) 1990, vol. 76, No. 4, pp. 579–584.

Harris E.T. et al., "The Effects of Estrone Ogen on Sprinal Bone Density of Postmenopausal Women" Arch Internal Medicine, vol. 151, No. 10, pp. 1980–1984, Oct. 1991.

*Primary Examiner*—James M. Spear
*Attorney, Agent, or Firm*—Pennie & Edmonds

[57] ABSTRACT

Oral water-soluble pharmaceutical compositions containing a therapeutically effective amount of a water-soluble and stable estrogen compound such as estropipate (piperazine estrone sulfate), and at least one water-soluble, pharmaceutically acceptable calcium salt in the presence of a suitable, pharmaceutically acceptable excipient. Compositions which include an organic acid and a calcium carbonate or bicarbonate compound which reacts with the organic acid when the composition is added to water to provide effervescence are preferred.

19 Claims, No Drawings

ORAL WATER SOLUBLE PHARMACEUTICAL COMPOSITIONS CONTAINING ESTRONE COMPOUND AND CALCIUM SALT

This application is a 371 of PCT/EP94/02465 filed Jul. 26, 1994.

TECHNICAL FIELD

The present invention relates to oral water soluble pharmaceutical compositions containing estrone derivative, useful for the substitutive hormonal therapy (hypoestrogenic) and in the prevention of the bone loss in the cases of senile or post-menopausal osteoporosis.

BACKGROUND ART

Estrone, the metabolite of estradiol, is used alone or in combination with other natural estrogens, in the form of ester (acetate, propionate) or as hydrosoluble conjugate (sodium or piperazine sulphate) in the substitutive hormonal therapy (hypoestrogenic) and in the prevention of the bone loss in the cases of post-menopausal Osteoporosis or in oophorectomized women.

The administration of estrone at therapeutical doses is effected both by oral route (tablets) and parenteral or transdermal route.

Estrogens are usually administered as oral tablets, the most common preparations being conjugated (equine) estrogens, micronized estradiol, and estrone piperazine sulfate (estropipate).

The oral administration of liquid compositions containing estrone presents some difficulties due to the insolubility in water of the compound, as well as of its esters. This problem can be solved by formulating the medicament in solid oral forms, but the problem of the incomplete absorption of the active ingredient at gastric level and of the possible difficulty of administering said forms to patients with poor swallowing capacity still remains.

It is well known that oral water soluble, liquid and optionally effervescent forms promote the absorption of the active ingredient, as for example in the case of aspirin, paracetamol, potassium, and others. Moreover, the liquid effervescent formulations result particularly appreciated to patients in view of their aspect and the possibility to give them good palatability.

For the preparation of liquid forms comprising estrone it is necessary to provide their hydrosoluble compounds. The alkali-conjugate estrone salts (sodium-sulfates) are hydrosoluble, but unstable in aqueous media, with the resulting precipitation of insoluble products.

In the bone-loss preventive therapy it is common practice to provide a calcium supplement to the patient. A large number of calcium preparations are available, including chewable tablets, ordinary oral tablets and even effervescent preparations.

The oral absorption of these available preparations is deemed to be satisfactory, although it can be variable depending on the nature of the calcium salt (carbonate, citrate, gluconate, lactate, phosphate, etc.). An extensive description of available calcium preparations can be found in the 3$^{rd}$ edition of Martindale, The Extra Pharmacopoeia, London, The Pharmaceutical Press, 1993, page 853 to 856.

If the skilled technician had thought to combine an estrogen derivative with a calcium salt in an oral, liquid composition, he would have faced some critical issues of pharmaceutical technology and pharmacology.

The estrogen component must be freely soluble in aqueous concentrated electrolyte solutions and stable, at neutral or basic pH, if the resulting pH of the liquid preparation is acidic, the estrogen component must be stable in a conjugate form (acid sulfate) even if present as a finely dispersed colloidal form, readily absorbed at intestinal pH.

The calcium preparations must be readily soluble in water giving a solution which should be clear or slightly cloudy but without insoluble residues, which, if formed, will not be completely absorbed.

The combination tablet or sachet must be pharmaceutically stable, particularly concerning the estrogen component and have an acceptable shelf-life.

The tablet or sachet must dissolve in water within a conveniently short time, preferably within a few minutes, to avoid hydrolysis of the estrogen component or precipitation of the calcium salts out of the saturated aqueous solution.

If needed, the effervescence during dissolution of the preparation should be moderate to avoid spraying the saturated solution on the wall of the container and therefore depositing an insoluble rim which could take the crucial estrogen component out of solution.

The ingredients of the formulation must not interfere with the accuracy of the analytical determination of the estrogen component which is present in very small amounts. In addition the final pH of the solution should be very close to 7 since higher pHs favour the precipitation of the calcium ingredient as calcium hydroxide and lower pHs will hydrolize the estrogen conjugate and give the less absorbable free estrone.

Finally, the preparation must have an acceptable or a pleasant taste for optimal patient compliance.

As far as the applicant is aware, there is no teaching in the prior art on how to solve all the above problems.

SUMMARY OF THE INVENTION

After a thorough experimentation, it has now surprisingly been found that the association between a water soluble and stable estrogen derivative and a pharmaceutically acceptable soluble salt of calcium allows the preparation of acceptable liquid and, if needed, effervescent pharmaceutical compositions which ensure a good absorption of the active ingredient when orally administered.

Therefore the object of the present invention are oral water soluble pharmaceutical compositions characterized in that they contain a combination of a water soluble and stable estrogen derivative and at least one soluble salt of calcium. Preferably, the compositions provided by the present invention are in the form of oral water soluble effervescent composition.

Said compositions, once added to a suitable amount of water, give complete drinkable solution within minutes.

DETAILED DESCRIPTION OF THE PREFERRED EMBODIMENTS

Advantageously, the presence of calcium ions in the compositions according to the invention yields a further therapeutical support to the action of estrone in the treatment of senile or post-menopausal osteoporosis. A further advantage of the present invention is to provide in a single pharmaceutical composition a twofold therapeutic action, the estrogenic one and the mineral one. A still further advantage of the present invention is to provide a drinkable solution, which ensures the optimal oral absorption of the active ingredients, at the same time providing a good compliance by the patient, especially by elder people having swallowing difficulties. Lastly, the present invention provides a pharmaceutical composition with a reduced cost of medication.

In a preferred embodiment of the invention calcium hydrogencarbonate is the calcium salt.

In a more preferred embodiment, calcium carbonate is the calcium salt.

In a even more preferred embodiment of the present invention, calcium glycerophosphate is the calcium salt. This last is preferred for its water solubility and high elemental calcium content and is also capable of providing a desiderable amount of phosphorus.

In a most preferred embodiment, estropipate is the estrogen derivative.

Estropipate has proved to be the most suitable estrogen derivative because of its water solubility and stability, contrarily to the much less stable conjugate equine estrogens or the insoluble non-conjugated estrogen preparations. It is however clear that other stable and suitable estrogen conjugates can be used such as the ammonium and substituted ammonium salts such as the tromethamine salt, the soluble succinate salts, the phosphate ester salts and similar pharmaceutically acceptable soluble derivatives well known to the skilled in the art.

The compositions of the present invention can be in the form of granulate or tablets.

Said compositions are prepared according to conventional techniques well known to the expert in the field, as de scribed for example in "Remington's Pharmaceutical Sciences Handbook" XVII Ed.; Mack pub. U.S.A..

As known, effervescence is obtained by means of a reaction in aqueous ambient between an acid and a carbonate or a bicarbonate.

The mostly used acids are citric, tartaric, fumaric and boric acid. Citric, tartaric and fumaric acid, particularly citric acid, which contributes to give an agreeable taste to the final solution, are preferred.

Among the carbonates usable according to the invention, those of sodium, potassium, lithium and calcium can be cited.

Calcium carbonate is more preferred, since it contemporaneously yields the calcium provided in the present invention and the source of $CO_2$ necessary for effervescence.

Whenever the expert in the field considered useful to use suitable excipients, such as binders, lubricants, sweetenings, aromatizing, dyes, this can be done however without departing from the scope of the present invention.

Examples of binders are sugars, glycine.

Examples of lubricants are benzoates, polyethylene glycols, leucine.

The process for the preparation of the compositions of the present inventions provides the work up in suitable conditions which avoids the early reaction between the acid and carbonate, in particular low humidity (35% maximum) and temperature (25° C. maximum) shall be controlled.

The pharmaceutical compositions according to the invention may be in the form of powders, granules, sachets, tablets, or in the form of liquid compositions, such as solutions.

Although the dosages are determined by the pathology kind, the conditions of the patient (age, sex, weight) and will be established by the skilled doctor, a dose range is indicated from 0.375 to 1.50 mg (corresponding to 0.3125 to 1.25 mg of sodium estrone sulfate).

The ratios among estropipate, calcium salt and other excipients which concur in the formulation of the soluble or effervescent compositions according to the present invention are not critical. In particular, estropipate and the calcium salt will be contained in the form of dosage unit in a therapeutically effective amount, whereas the expert in the field will easily be capable of determining the ratio between the acid and the carbonate, or bicarbonate, as to assure a good effervescence and rapid dissolution of the pharmaceutical composition.

EXAMPLES

The following examples further illustrate the present invention.

Example 1

For 10,000 effervescent tablets the following ingredients were used:

17.22 kg of granular calcium carbonate
5.20 kg of granular citric acid
3.05 kg of granular fumaric acid
7.50 g of estropipate (estrone sulphate of piperazine 1:1)
1.00 kg of leucine hydrochloride
50 g of soluble flavours
50 g of calcium ciclamate.

The ingredients were put in a mixer (P-K twin-shell blender, or the like) and mixed for 20 minutes. The mixture was tabletted, granulated and sieved (16 mesh).

The sieved granulate was tabletted in an atmosphere with less than 30% of humidity at the temperature of 20° C. to give 10,000 effervescent tablets.

The above amounts can be modified according to the desired posology of estrone or elemental calcium, by varying, if necessary also the amount of citric acid necessary for effervescence.

Example 2

For 10,000 effervescent tablets the following ingredients were used:

52.50 kg of calcium glycerophosphate
22.30 kg of saccharose
1.00 kg of PEG 6000
7.50 g of estropipate (estrone sulphate of piperazine 1:1)
0.10 kg of silicon dioxide
0.10 kg of magnesium stearate
1.50 kg of leucine
1.70 kg of citric acid
5.00 kg of aspartame
5.00 kg of sodium bicarbonate.

The ingredients were worked according to the procedure of Example 1 to give 10,000 effervescent tablets.

Example 3

10,000 non effervescent sachets were prepared with the ingredients shown in Example 2, except silicon dioxide and magnesium stearate, citric acid and sodium bicarbonate.

Example 4

Oral liquid pharmaceutical compositions were prepared according to conventional techniques with the following unitary composition:

| | |
|---|---|
| Calcium glycerophosphate | 5.250 g |
| Saccharose | 2.230 g |
| PEG 6000 | 0.100 g |
| Estropipate | 0.750 mg |
| Leucine | 0.150 g |

|   |   |
|---|---|
| Aspartame | 0.050 mg |
| Distilled water | 100 g. |

Example 5

Oral effervescent pharmaceutical compositions were prepared according to the above examples with the following unitary composition:

|   |   |
|---|---|
| Estropitate | 0.75 mg |
| Ca glycerophosphate | 5.250 g |
| Citric acid | 0.5 g |
| Sodium bicarbonate | 0.658 mg |
| Sucrose | 4.000 g |
| Aspartame | 0.04 g |
| Aroma (orange) | 0.05 g. |

For all the above examples it is understood that flavouring agents colorants and aroma can be added according to conventional practice.

The above amounts can be modified according to the desired posology of estrone or elemental calcium, by varying, if necessary also the amount of citric acid necessary for effervescence.

What is claimed is:

1. An oral water soluble pharmaceutical composition containing a therapeutically effective amount of a water-soluble and stable estrogen compound and at least one water-soluble, pharmaceutically acceptable calcium salt of calcium glycerophosphate or calcium hydrogen carbonate in the presence of a suitable, pharmaceutically acceptable excipient.

2. The composition according to claim 1, characterized in that the estrogen compound is estropipate (piperazine estrone sulfate).

3. The composition according to claim 1, characterized in that calcium glycerophosphate is the calcium salt.

4. An oral water-soluble pharmaceutical composition containing a therapeutically effective amount of a water-soluble and stable estrogen compound, and first and second water-soluble, pharmaceutically acceptable calcium salts in the presence of a suitable, pharmaceutically acceptable excipient.

5. The compositions according to claim 1, characterized in that calcium hydrogencarbonate is the calcium salt.

6. The composition according to claim 4, characterized in that the estrogen compound is estropipate (piperazine estrone sulfate).

7. An effervescent, oral, water-soluble pharmaceutical composition containing a therapeutically effective amount of a water-soluble and stable estrogen compound and at least one water-soluble calcium salt in the presence of a suitable, pharmaceutically acceptable excipient.

8. The compositions according to claim 1 in the form of powders, granulates, tablets or a liquid.

9. Oral effervescent pharmaceutical compositions according to claim 7 in the form of tablets having the following unitary composition:

|   |   |
|---|---|
| calcium glycerophosphate | 5.250 g |
| saccharose | 2.230 g |
| PEG 6000 | 0.100 g |
| estropipate (estrone sulphate of piperazine 1:1) | 0.750 mg |
| silicon dioxide | 0.010 g |
| magnesium stearate | 0.010 g |
| leucine | 0.150 g |
| citric acid | 1.700 g |
| aspartame | 0.050 g |
| sodium bicarbonate | 0.500 g. |

10. Oral effervescent pharmaceutical compositions according to claim 7 in the form of tablets having the following unitary composition:

|   |   |
|---|---|
| Calcium carbonate granular | 1.722 g |
| Citric acid granular | 0.520 g |
| Fumaric acid granular | 0.305 g |
| Estropipate | 0.750 mg |
| Leucine hydrochloride | 0.10 g |
| Soluble flavours | 5.0 mg |
| Calcium ciclamate | 5.0 mg. |

11. Oral water soluble pharmaceutical compositions according to claim 8 in the form of granules or powder or sachets having the following unitary composition:

|   |   |
|---|---|
| Calcium glycerophosphate | 5.250 g |
| Saccharose | 2.230 g |
| PEG 6000 | 0.100 g |
| Estropipate | 0.375 mg |
| Leucine | 0.150 g |
| Aspartame | 0.050 mg |

12. Oral liquid pharmaceutical compositions according to claim 8 of the following unitary composition:

|   |   |
|---|---|
| Calcium glycerophosphate | 5.250 g |
| Saccharose | 2.230 g |
| PEG 6000 | 0.100 g |
| Estropipate | 0.750 mg |
| Leucine | 0.150 g |
| Aspartame | 0.050 mg |
| Distilled water | 100 g |

13. The composition of claim 7 wherein the water soluble calcium salt comprises an organic acid and a calcium carbonate or bicarbonate compound which reacts with the organic acid when the composition is added to water.

14. The composition of claim 13 where the organic acid is citric acid, the calcium compound is calcium carbonate and the estrogen compound is estropipate (piperazine estrone sulfate).

15. The composition of claim 7 which includes an organic acid and a carbonate or bicarbonate compound which reacts with the organic acid when the composition is added to water to provide effervescence.

16. The composition of claim 15 wherein the organic acid is citric, tartaric or fumaric acid, the carbonate or bicarbonate compound is a sodium, potassium, lithium or calcium carbonate, and the estrogen compound is estropipate (piperazine estrone sulfate).

17. The composition according to claim 7, in the form of powders, granulates, tablets or a liquid.

18. The composition according to claim 4, characterized in that calcium salts include calcium glycerophosphate, calcium hydrogen carbonate, or the reaction product of calcium carbonate or bicarbonate with an organic acid.

19. The composition according to claim 4, in the form of powders, granulates, tablets or a liquid.

* * * * *